US007732637B2

(12) United States Patent
Maezono et al.

(10) Patent No.: US 7,732,637 B2
(45) Date of Patent: Jun. 8, 2010

(54) ACYLAMIDE COMPOUNDS HAVING SECRETAGOGUE OR INDUCER ACTIVITY OF ADIPONECTIN (75) Inventors: Katsumi Maezono, Kawasaki (JP); Toshihiko Yoshimura, Kawasaki (JP); Nozomu Ishida, Kawasaki (JP); Naoyuki Fukuchi, Kawasaki (JP); Toshihiro Hatanaka, Kawasaki (JP); Osamu Ikehara, Kawasaki (JP); Yayoi Kawato, Kawasaki (JP); Hideyuki Tanaka, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 11/835,029

(22) Filed: Aug. 7, 2007

(65) Prior Publication Data
US 2007/0282002 A1 Dec. 6, 2007

Related U.S. Application Data (63) Continuation of application No. PCT/JP2006/302058, filed on Feb. 7, 2006.

(30) Foreign Application Priority Data
Feb. 7, 2005 (JP) ............................. 2005-030828

(51) Int. Cl.
C07C 229/06 (2006.01)
A61K 31/20 (2006.01)
(52) U.S. Cl. .................. 562/567; 554/63; 514/563; 514/625
(58) Field of Classification Search ............ 564/35, 564/36; 514/558, 563
See application file for complete search history.

(56) References Cited

U.S. PATENT DOCUMENTS

| 5,266,576 | A | 11/1993 | Vincent et al. |
| 6,090,250 | A * | 7/2000 | Mazzeo et al. ............. 204/451 |
| 6,335,468 | B1 | 1/2002 | Hatajima et al. |

FOREIGN PATENT DOCUMENTS

| JP | 29-6713 | 10/1954 |
| JP | 05-132454 | 5/1993 |
| JP | 9-503295 | 3/1997 |
| JP | 2001-187769 | 7/2001 |

OTHER PUBLICATIONS

Philipp E. Scherer, et al., "A Novel Serum Protein Similar to C1q. Produced Exclusively in Adipocytes", The Journal of Biological Chemistry, vol. 270, 45 Issue of Nov. 10, pp. 26746-26749, 1995.
Erding Hu, et al., "Adipoq is a Novel Adipose-Specific Gene Dysregulated in Obesity", The Journal of Biological Chemistry, vol. 271, No. 18, Issue of May 3, p. 10697-10703, 1996.
Makoto Daimon, et al., "Decreased Serum Levels of Adiponectin are a Risk Factor for the Progression to Type 2 Diabetes in the Japanese Population", Epidemiology/ Health Services/Psychosocial Research, Diabetes Care, vol. 26, No. 7, Jul. 2003.
T. Yamauchi, et al., "The Fat-Derived Hormone Adiponectin Reverses Insulin Resistance Associated With Both Lipoatrophy and Obesity", Nature Medicine. vol. 7, No. 8, Aug. 2001, pp. 941-946.
Anders H. Berg, et al., "The Adipocyte-Secreted Protein ACRP 30 Enhances Hepatic Insulin Action" Nature Medicine, vol. 7, No. 8, Aug. 2001, pp. 947-953.
Yoshihisa Okamoto, et al., "Circulation" American Heart Association, Learn and Live, Journal of the American Heart Association, Downloaded from Circ.ahajournals.org at Ajinomoto Co Inc on Apr. 30, 2007.
Yoshihiro Kamada, et al., "Basic-Liver, Pancreas, and Biliary Tract", Gastroenterology 2003, 125, pp. 1796-1807.
Takayuki Masaki, et al., "Adiponectin Protects LPS-Induced Liver Injury Through Modulation of TNF-α in KK-Ay Obese Mice", Hepatology, vol. 40, No. 1, 2004, pp. 117-184.
E. Jungermann, et al., "The Preparation of Long Chain N-Acylamino Acids", vol. 78, pp. 172-174.
Uzi Beitler, et al., "Interaction Between Asymmetric Solutes and Solvents Diamides Derived From L-Valine as Stationary Phases in Gas-Liquid Partition Chromatography", Journal of chromatography, 123 (1976), pp. 149-166.
R. Charles, et al., "Separation of Enantiomers on Packed Columns Containing Optically Active Diamide Phases"; Journal of Chromatography, 112 (1975), pp. 121-133.

* cited by examiner

Primary Examiner—Shailendra Kumar
(74) Attorney, Agent, or Firm—Oblon, Spivak, McClelland, Maier & Neustadt, L.L.P.

(57) ABSTRACT

The present invention provides an acylamide compound of the following formula (1), prodrugs thereof, or pharmaceutically acceptable salts thereof; and an adiponectin inducer or secretagogue, therapeutic agent of metabolic syndromes, therapeutic agent of hypoadiponectinemia, therapeutic agent of hyperlipemia, preventive/therapeutic agent of diabetes, improving agent of impaired glucose tolerance, improving agent of insulin resistance, enhancing agent of insulin sensitivity, therapeutic agent of hypertension, preventive/therapeutic agent of vascular disorders, an anti-inflammatory agent, therapeutic agent of hepatic inflammation, therapeutic agent of fatty liver, therapeutic agent of hepatic fibrosis, therapeutic agent of liver cirrhosis, preventive/therapeutic agent of non-alcoholic/nonviral steatohepatitis (NASH) or non-alcoholic/nonviral fatty liver disease (NAFLD), or therapeutic agent of obesity, each of which has the above compounds as an active ingredient.

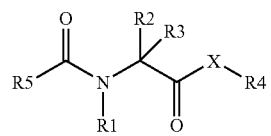

Formula (1)

6 Claims, 3 Drawing Sheets

FIG.1

☐ 2 days before admin.
▨ 6 days after admin.
▩ 14 days after admin.
▨ 26 days after admin.

ACYLAMIDE COMPOUNDS HAVING SECRETAGOGUE OR INDUCER ACTIVITY OF ADIPONECTIN

This application is a CON of PCT/JP2006/302058, filed Feb. 7, 2006.

TECHNICAL FIELD OF THE INVENTION

The present invention relates to adiponectin inducers or secretagogues, and preventive/therapeutic agents of various diseases by making use of the secretagogue or inducer of adiponectin. More specifically, it relates to acylamide compounds having secretagogue or inducer activity of adiponectin.

BACKGROUND OF THE INVENTION

Among the diseases widely called as adult diseases (diseases in persons of middle or advanced age) or life-style related diseases, those such as abnormal carbohydrate/lipid metabolisms; impaired glucose tolerance, diabetes, hyperlipemia and high-blood pressure related thereto; and abdominal obesity form clusters of the diseases that are recognized as metabolic syndromes. Patients with metabolic syndromes not only have a low quality of life due to the various symptoms but also have higher lethal risk or a risk of developing fatal vascular disorders such as arterial sclerosis as compared with healthy people. The diseases or symptoms such as impaired glucose tolerance, diabetes, hyperlipemia and high-blood pressure are just the tip of the iceberg of metabolic syndromes as a whole. Though it is important to provide the treatment corresponding to each disease/symptom, it is thought that the most effective method to diminish a lethal risk is to prevent/treat overall syndromes by preventing/treating abnormalities that deeply relate to the pathogenic mechanism of metabolic syndromes. Nevertheless, such therapeutic agents and/or therapeutic methods have not yet been found until now.

Through the achievement of the recent multicenter studies, the abnormalities relating to adiponectin that is expressed/generated in adipose tissues and secreted in the blood are paid attention as the most important cause of metabolic syndromes. Adiponectin was found as a secreted protein that is specifically expressed in adipose tissues and has a similar structure to that of complements (Non-patent Literatures 1 and 2). Patients with metabolic syndromes develop hypoadiponectinemia and, for example, it is reported that hypoadiponectinemia is a risk factor independent of other factors of type II diabetes (Non-patent Literature 3). In addition to the diseases such as metabolic syndromes and those that relate to abnormal carbohydrate metabolism, e.g. diabetic retinopathy, gestational diabetes mellitus and polycystic ovary syndrome, hypoadiponectinemia or the decreased expression of adiponectin mRNA in tissues is reported in the diseases such as cardiovascular diseases, e.g. ischemic heart disease, myocardial infarction, angina pectoris, vascular stenosis, and hypertrophic cardiomyopathy; vascular diseases, e.g. coronary artery heart disease, coronary artery disease, cerebrovascular disorder and peripheral artery disease; liver diseases, e.g. hepatic fibrosis, liver cirrhosis, hepatic inflammation, non-alcoholic/nonviral steatohepatitis and fatty liver disease (NASH and NAFLD), alcoholic fatty liver and alcoholic hepatic disorder; cancers/malignant neoplasm, e.g. endometrioma, uterine leiomyoma and lung cancer; endocrine/metabolic diseases, e.g. Cushing's syndrome, HIV-related lipodystrophy syndrome, thyroidal dysfunction and atrophy of adipose tissues; and neurogenic emaciation, bulimia nervosa, and nephropathy. It is also reported, including the reports in the level of basic experiments, that the development of the diseases due to lack of adiponectin is seen and there is a possibility of treatment by supplying adiponectin.

Particularly, in the level of the basic experiments, effects of decreasing lipids in the blood and blood glucose and preventing body weight gain are seen in model animals by administering recombinant adiponectin, and, therefore, its possibility as a therapeutic agent of metabolic syndromes is reported (Non-patent Literatures 4 and 5). Besides it, it is also reported that adiponectin has an anti-atherogenic action acting directly to blood vessels, such as effects of: inhibiting foaming or adhesion of monocytes; inhibiting proliferation of smooth muscle cells; and inhibiting intimal thickening (Non-patent Literature 6). Further, its possibility as a therapeutic agent of hepatic diseases is also reported since it inhibits: hepatic fibrosis in the disease models induced by chemical substances; activation of stellate cells that play a large part of hepatic fibrosis; hepatic inflammation induced by endotoxin, and the like (Non-patent Literatures 7 and 8). It is also reported that adiponectin has an anti-inflammatory action, and it is paid attention as a therapeutic agent that mimics exercise effects, since adiponectin induces 5'AMP-activated kinase activity to tissues, said activity which is induced during exercise and considered to be important in the molecular mechanism that brings exercise benefits. Thus, adiponectin is paid attention as a preventive/therapeutic agent of various fatal diseases. However, administration method of adiponectin to patients is expected to be injection just as the method of physiologically active substances such as insulin, and it is a therapeutic method with pain and time-consuming. Therefore, in the present situation, it is desired to develop a therapeutic agent such as those that can induce expression of adiponectin by directly acting on adipose cells and increase its secretion in the blood.

Non-patent Literature 1: A novel serum protein similar to C1q, produced exclusively in adipocytes. J Biol Chem 1995 Nov. 10; 270(45):26746-9

Non-patent Literature 2: AdipoQ is a novel adipose-specific gene dysregulated in obesity. J Biol Chem 1996 May 3; 271 (18):10697-703

Non-patent Literature 3: Decreased serum levels of adiponectin are a risk factor for the progression to type 2 diabetes in the Japanese Population: the Funagata study. Diabetes Care 2003 July; 26(7):2015-20

Non-patent Literature 4: The fat-derived hormone adiponectin reverses insulin resistance associated with both lipoatrophy and obesity. Nat. Med. 2001 August; 7(8):941-6

Non-patent Literature 5: The adipocyte-secreted protein Acrp30 enhances hepatic insulin action. Nat. Med. 2001 August; 7(8):947-53

Non-patent Literature 6: Adiponectin reduces atherosclerosis in apolipoprotein E-deficient mice. Circulation. 2002 Nov. 26; 106(22):2767-70

Non-patent Literature 7: Enhanced carbon tetrachloride-induced liver fibrosis in mice lacking adiponectin. Gastroenterology. 2003 December; 125(6):1796-807

Non-patent Literature 8: Adiponectin protects LPS-induced liver injury through modulation of TNF-alpha in KK-Ay obese mice. Hepatology. 2004 July; 40(1):177-84

DISCLOSURE OF THE INVENTION

The object of the present invention is to provide novel compounds, which have an inducing action of expression of adiponectin in tissues and a secretagogue action thereof into the blood.

The further object of the present invention is to provide adiponectin inducers or secretagogues, which have an inducing action of expression of adiponectin in tissues and a secretagogue action thereof into the blood.

The additional object of the present invention is to provide therapeutic agents of metabolic syndromes.

The further additional object of the present invention is to provide therapeutic agents of hypoadiponectinemia or hyperlipemia; preventive/therapeutic agents of diabetes; improving agents of impaired glucose tolerance or insulin resistance; enhancing agents of insulin sensitivity; therapeutic agents of hypertension; preventive/therapeutic agents of vascular disorders; or anti-inflammatory agents.

The further additional object of the present invention is to provide therapeutic agents of hepatic inflammation, fatty liver, hepatic fibrosis or liver cirrhosis; preventive/therapeutic agents of non-alcoholic/nonviral steatohepatitis (NASH) or non-alcoholic/nonviral fatty liver disease (NAFLD); or therapeutic agents of obesity.

The further additional object of the present invention is to provide foods and beverages that comprise the adiponectin inducer(s) or secretagogue(s).

The further additional object of the present invention is to provide foods and beverages on which it is indicated to have the above medicinal effects.

The inventors searched, among the cells holding the features of fat well, a substance(s) that increase the secretion of adiponectin and the adiponectin concentration in the culture solution, and found that specific acylamide compounds increase secretion of adiponectin or are necessary for its secretion. Especially, the present invention has been completed based on the finding that the above compounds are highly useful for patients with hypoadiponectinemia or the decreased expression of adiponectin mRNA.

Namely, the present invention provides an acylamide compound of the formula (1), prodrugs thereof, or pharmaceutically acceptable salts thereof:

Formula (1)

wherein R1 is a hydrogen atom or an alkyl group having 1 to 6 carbon atoms;

R2 is an alkyl group having 1 to 10 carbon atoms, aryl group having 6 to 10 carbon atoms, heteroaryl group having 1 to 10 carbon atoms, arylalkyl group having 7 to 20 carbon atoms, heteroarylalkyl group having 2 to 11 carbon atoms or alkylthioalkyl group having 2 to 6 carbon atoms;

R3 is a hydrogen atom or an alkyl group having 1 to 6 carbon atoms, and R2 and R3 may bond each other to form a ring;

R4 is a hydrogen atom or an alkyl group having 1 to 16 carbon atoms;

R5 is a straight-chain hydrocarbon group having 5 to 21 carbon atoms which may have 1 to 3 double bond(s); and X is an oxygen atom or NH.

The present invention also provides an adiponectin inducer or secretagogue or a therapeutic agent of metabolic syndromes, which comprises the above acylamide compound, prodrugs thereof, or pharmaceutically acceptable salts thereof.

The present invention further provides a therapeutic agent of hypoadiponectinemia or hyperlipemia; a preventive/therapeutic agent of diabetes; an improving agent of impaired glucose tolerance or insulin resistance; an enhancing agent of insulin sensitivity; a therapeutic agent of hypertension; a preventive/therapeutic agent of vascular disorders; an anti-inflammatory agent; a therapeutic agent of hepatic inflammation, fatty liver, hepatic fibrosis or liver cirrhosis; a preventive/therapeutic agent of non-alcoholic/nonviral steatohepatitis (NASH) or non-alcoholic/nonviral fatty liver disease (NAFLD); or a therapeutic agent of obesity, which comprises the above acylamide compound, prodrugs thereof, or pharmaceutically acceptable salts thereof.

The present invention additionally provides a food and beverage comprising the above acylamide compound, prodrugs thereof, or pharmaceutically acceptable salts thereof, on which it is indicated to have an effect of preventing/treating hypoadiponectinemia, hyperlipemia or diabetes; an effect of improving impaired glucose tolerance or insulin resistance; an effect of enhancing insulin sensitivity; an effect of preventing/treating hypertension or vascular disorders; an effect of preventing/treating fatty liver or hepatic fibrosis; a therapeutic effect on liver cirrhosis; or an effect of preventing/treating non-alcoholic/nonviral steatohepatitis (NASH), non-alcoholic/nonviral fatty liver disease (NAFLD) or obesity.

BEST MODE FOR CARRYING OUT THE INVENTION

Regarding the acylamide compounds of the formula (1), in the formula (1), an alkyl group includes a straight-chain, branched-chain or cyclic alkyl group. It may have a substituent(s) such as a halogen atom and a hydroxyl group, but an alkyl group without these substituents is preferable.

An aryl group represents a mono-, bi- or tri-cyclic aromatic substituent composed of carbon atoms and preferably a mono- or bi-cyclic aromatic substituent. Its examples include a phenyl group, indenyl group, naphthyl group and fluorenyl group, and a phenyl group is preferable. An aryl group may have a substituent(s) such as a lower alkyl group, lower alkoxy group, a halogen atom and a hydroxyl group.

A heteroaryl group represents an aromatic heterocyclic substituent consisting of 1 to 3 ring(s) each comprising 5 to 7 members of carbon and nitrogen, oxygen, sulfur or the like. For example, it includes a pyridyl group, pyridazinyl group, pyrimidinyl group, pyrazinyl group, pyrrolyl group, furanyl group, thienyl group, oxazolyl group, isoxazolyl group, pyrazolyl group, imidazolyl group, thiazolyl group, isothiazolyl group, thiadiazolyl group, indolyl group, isoindolyl group, benzofuryl group, isobenzofuryl group, benzothienyl group, benzopyrazolyl group, benzoimidazolyl group, benzoxazolyl group, benzothiazolyl group, quinolyl group, isoquinolyl group, naphthyridinyl group and quinazolyl group.

An arylalkyl group indicates an alkyl group substituted with one or more aryl group(s), and the substitution position thereof is not particularly limited.

An alkyl group in an arylalkyl group, heteroarylalkyl group and alkylthioalkyl group is preferably a straight- or branched-chain alkyl group. Examples of an aryl group in the arylalkyl group are those mentioned in the above "aryl group", and specifically a phenyl group. Examples of a heteroaryl group in the heteroarylalkyl group are those mentioned in the above "heteroaryl group."

Examples of a straight-chain hydrocarbon group include a straight-chain alkyl group, straight-chain alkenyl group and straight-chain alkynyl group. A straight-chain alkenyl group preferably has one or two unsaturated bond(s) in the molecule. These straight-chain hydrocarbon groups may have a substituent(s) such as a halogen atom and a hydroxyl group, but those without these substituents are preferable.

In the formula (1), R1 is preferably a hydrogen atom or an alkyl group having 1 to 4 carbon atoms; and said alkyl group is preferably a straight or branched chain, and particularly preferably a straight-chain alkyl group.

R2 is preferably an alkyl group having 1 to 6 carbon atoms, phenylalkyl group having 7 to 11 carbon atoms or alkylthioalkyl group having 2 to 6 carbon atoms. Further, R2 is preferably an alkyl group having 1 to 4 carbon atoms, phenylalkyl group having 7 to 8 carbon atoms or alkylthioalkyl group having 2 to 4 carbon atoms. Here, the alkyl group is preferably a straight or branched chain.

R3 is preferably a hydrogen atom or an alkyl group having 1 to 4 carbon atoms. Here, the alkyl group is preferably a straight or branched chain.

Here, in the formula (1), it is preferable that a structural part to which R1 R3 are attached is derived from an amino acid selected from the group consisting of Ile, Leu, Val, Phe, Ala and Met. It is further preferable that it is derived from a DL- or L-amino acid. Among them, it is particularly preferable that it is derived from an L-amino acid.

R4 is preferably a hydrogen atom, a straight- or branched-chain alkyl group having 1 to 4 carbon atoms, cyclic alkyl group having 3 to 8 carbon atoms, or straight- or branched-chain alkyl group having 10 to 16 carbon atoms.

R5 is preferably a straight-chain alkyl group having 5 to 21 carbon atoms or alkenyl group which has one or two double bond(s).

Further, in the present invention,

[2] it is preferable in the formula (1) that R1 is a hydrogen atom or an alkyl group having 1 to 4 carbon atoms; R2 is a straight- or branched-chain alkyl group having 1 to 4 carbon atoms, phenylalkyl group having 7 to 8 carbon atoms or alkylthioalkyl group having 2 to 4 carbon atoms; R3 is a hydrogen atom or an alkyl group having 1 to 4 carbon atoms; R4 is a hydrogen atom or an alkyl group having 1 to 4 carbon atoms; R5 is a straight-chain alkyl group having 5 to 21 carbon atoms which may have one double bond; and X is an oxygen atom.

[3] In above [2], it is preferable that R1 is a hydrogen atom or an alkyl group having 1 to 4 carbon atoms; R2 is a straight- or branched-chain alkyl group having 1 to 4 carbon atoms, phenylalkyl group having 7 to 8 carbon atoms or alkylthioalkyl group having 2 to 4 carbon atoms; R3 is a hydrogen atom; R4 is a hydrogen atom; and R5 is a straight-chain alkyl group having 5 to 21 carbon atoms which may have one double bond.

[4] In above [2], it is preferable that R1 is a hydrogen atom or an alkyl group having 1 to 4 carbon atoms; R2 is a straight- or branched-chain alkyl group having 1 to 4 carbon atoms, phenylalkyl group having 7 to 8 carbon atoms or alkylthioalkyl group having 2 to 4 carbon atoms; R3 is an alkyl group having 1 to 4 carbon atoms; R4 is a hydrogen atom; and R5 is a straight-chain alkyl group having 5 to 21 carbon atoms which may have one double bond.

[5] It is preferable in the formula (1) that R1 is a hydrogen atom or an alkyl group having 1 to 4 carbon atoms; R2 is a straight- or branched-chain alkyl group having 1 to 4 carbon atoms; R3 is a hydrogen atom; R4 is a hydrogen atom or a straight-chain, branched-chain or cyclic alkyl group having 1 to 16 carbon atoms; R5 is a straight-chain alkyl group having 5 to 21 carbon atoms which may have one double bond; and X is NH.

The present invention preferably comprises acylamide compounds of the following structural formulae, prodrugs thereof, or pharmaceutically acceptable salts thereof:

Formula 2

Formula 3

Formula 4

Formula 5

Formula 6

Formula 7

Formula 8

Formula 9

Formula 10

Formula 11

-continued

Formula 12

Formula 13

Formula 14

Formula 15

Formula 16

Formula 17

Formula 18

When the acylamide compounds of the present invention can form salts thereof, it is sufficient for the salts to be pharmaceutically accepted ones and preferably medicinally acceptable ones. For example, to an acidic group(s) in case that the acidic group(s) exists in the acylamide compound, the examples include ammonium salts, and salts with alkali metals, e.g. sodium and potassium, salts with alkaline earth metals, e.g. calcium and magnesium, salts with aluminum and zinc, salts with organic amines, e.g. triethylamine, ethanolamine, morpholine, piperidine and dicyclohexylamine, and salts with basic amino acids, e.g. arginine and lysine. To a basic group(s) in case that the basic group(s) exists in the acylamide compound, the examples include salts with inorganic acids, e.g. a hydrochloric acid, sulfuric acid and phosphoric acid, salts with organic carboxylic acids, e.g. an oxalic acid, acetic acid, citric acid, malic acid, benzoic acid, maleic acid, fumaric acid, tartaric acid, succinic acid and glutamic acid, and salts with organosulfonic acids, e.g. a methanesulfonic acid and p-toluenesulfonic acid. The salts can be formed by mixing the compound with a necessitated acid or base in a proper ratio in a solvent or dispersant, or by the cation exchange or anion exchange with another salt.

The compounds of the present invention include solvates thereof such as hydrates and alcohol adducts thereof. In addition, the compounds of the present invention also include prodrugs thereof.

Among the compounds of the formula (1), an N-acylamino acid wherein X is an oxygen atom can be produced, for example, by reacting a corresponding amino acid with an acid chloride(s) as mentioned in Japanese Patent Unexamined Publication No. Sho 29-006713 or J. Am. Chem. Soc., vol. 78, p. 172 (1956).

Further, among the compounds of the formula (1), N-acylamino-acid amides wherein X=NHR can be produced, for example, by reacting an active ester of a corresponding carboxylic acid with amino-acid amides, or by reacting an active ester of an N-acylamino acid with amines as mentioned in J. Chromatography, vol. 123, p. 149 (1976) or J. Chromatography, vol. 112, p. 121 (1975).

Meanwhile, any methods for producing the compounds of the formula (1) are not limited to the above illustrated production methods.

The present invention provides an adiponectin inducer or secretagogue or a therapeutic agent of metabolic syndromes, which comprises the above acylamide compound(s), prodrugs thereof, or pharmaceutically acceptable salts thereof.

The present invention also provides a therapeutic agent of hypoadiponectinemia or hyperlipemia; a preventive/therapeutic agent of diabetes; an improving agent of impaired glucose tolerance or insulin resistance; an enhancing agent of insulin sensitivity; a therapeutic agent of hypertension; a therapeutic agent of vascular disorders; an anti-inflammatory agent; a therapeutic agent of hepatic inflammation, fatty liver, hepatic fibrosis or liver cirrhosis; a preventive/therapeutic agent of non-alcoholic/nonviral steatohepatitis (NASH) or non-alcoholic/nonviral fatty liver disease (NAFLD); or a therapeutic agent of obesity, which comprises the above acylamide compound(s), prodrugs thereof, or pharmaceutically acceptable salts thereof.

The present invention further provides a food and beverage comprising the above acylamide compound(s), prodrugs thereof, or pharmaceutically acceptable salts thereof, on which it is indicated to have an effect of preventing/treating hypoadiponectinemia, hyperlipemia or diabetes; effect of improving impaired glucose tolerance or insulin resistance; an effect of enhancing insulin sensitivity; an effect of preventing/treating hypertension or vascular disorders; an effect of preventing/treating fatty liver or hepatic fibrosis; a therapeutic effect on liver cirrhosis; or an effect of preventing/treating non-alcoholic/nonviral steatohepatitis (NASH), non-alcoholic/nonviral fatty liver disease (NAFLD) or obesity.

In the present invention, it is possible to combine the acylamide compounds of the present invention, prodrugs thereof, or pharmaceutically acceptable salts thereof with the therapeutic agents of the above diseases. It may be a single preparation obtained by formulating the therapeutic agent of the present invention and the other therapeutic agent(s) simultaneously, or the combination of at least two kinds of preparations obtained by formulating the therapeutic agent of the present invention and the other therapeutic agent(s) separately. Examples of the therapeutic agents combined with the compounds of the present invention are antidiabetic agents such as insulin preparations, e.g. NPH, Lente and Ultralente; insulin derivatives, e.g. lispro; insulin secretagogues such as sulfonylurea agents, e.g. tolbutamide, chlorpropamide, glibenclamide, glipizide, glimepiride and gliclazide, or glinides, e.g. repaglinide, nateglinide, meglitinide and mitiglinide; insulin resistance improvers such as peroxisome proliferator activator receptor (PPAR)-γ agonists, e.g. pioglitazone, rosiglitazone, ciglitazone and troglitazone; biguanides, e.g. metformin, phenformin and buformin; α-glucosidase inhibitors, e.g. voglibose, acarbose and miglitol; glucagon-like peptide 1 (GLP1), GLP1 agonists, e.g. exenatide; GLP1 analogues; and dipeptidyl peptidase IV inhibitors, e.g. vildagliptin, sitagliptin and saxagliptin.

In addition to the above-mentioned antidiabetic agents, it is included in the present invention to combine the acylamide compounds of the present invention with the other agents of the diseases mentioned in the present invention, for example, therapeutic agents of hyperlipemia such as agents of cholaneresis and lipid absorption inhibitors such as hydroxymethyl glutaryl coenzyme A reductase inhibitors, e.g. pravastatin, simvastatin, fluvastatin, and atorvastatin, fibrate agents e.g. clofibrate, benzafibrate and simfibrate, and lipase inhibitors, e.g. orlistat; and therapeutic agents of hypertension such as angiotensin-converting enzyme inhibitors, angiotensin II receptor antagonists, β-receptor antagonists, α1-antagonists and calcium antagonists. As for its ratio in combination, it depends on various factors such as the intended administered dose and a used pharmaceutically acceptable carrier(s), and it can change widely.

In the present invention, preferably about 0.001 to 10000 mg and more preferably about 0.1 to 1000 mg of the acylamide compound can be contained per one preparation. The administered dose differs based on symptoms and age of the administered patient and the administration method, and, in general, 0.1 to 1000 mg/kg/day is preferable.

The administered form of the preventive/therapeutic agents of the present invention is not particularly limited. The safe and necessary amount thereof can be administered at once or via drip intravenously, intra-arterially, subcutaneously, intramuscularly, or by infusion. Either parenteral or oral administration is possible and the oral administration is preferable from the viewpoint of consideration to patients' pain.

The preventive/therapeutic agents of the present invention can be formulated into various dosage forms, e.g., in the case of oral agents, dosing preparations such as tablets, capsules, granules, dispersants, troches, solutions, subtle granules, injection solvents, cream pharmaceuticals and suppositories. The preparation thereof can be conducted by publicly known methods. Either the active ingredient of the present invention or its preparation may contain pharmaceutically acceptable carriers, diluents, excipients, disintegrating agents, lubricants, flow improvers, or other necessary substances as the preparation. The preparation can be produced by prescribing them, by combination thereof, if necessary. Examples of the preparation carriers include lactose, glucose, D-mannitol, starch, crystalline cellulose, calcium carbonate, kaolin, gelatin, hydroxypropyl cellulose, hydroxypropyl methyl cellulose, polyvinylpyrrolidone, ethanol, carboxy methyl cellulose, carboxy methyl cellulose calcium salts, magnesium stearate, talc, acetyl cellulose, sucrose, titanium oxide, benzoic acid, sodium dehydroacetate, gum arabic, tragacanth, methyl cellulose, egg yolk, surfactants, simple syrup, citric acid, distilled water, ethanol, glycerin, propylene glycols, macrogol, monobasic sodium phosphate, dibasic sodium phosphate, sodium phosphate, sodium chloride, phenol, thimerosal, p-hydroxybenzoate ester and acid sodium sulfite. They are used by being mixed with the compounds of the present invention depending on the dosage forms.

The present invention is useful for mammals such as mice, rats, hamsters, rabbits, felines, canines, bovines, sheep, apes and humans as preventive/therapeutic agents of various symptoms derived from hypoadiponectinemia or the decreased expression of adiponectin. Further, the present invention includes commercial packages, including descriptions wherein the acylamide compounds of the present invention should be used.

The acylamide compounds of the formula (1), prodrugs thereof, or pharmaceutically acceptable salts thereof having secretagogue or inducer activity of adiponectin are expected to have effects that existing therapeutic agents do not have, in that said compounds increase adiponectin in the body of the patient, and said adiponectin which is paid attention as a preventive/therapeutic agent of various fatal diseases. Thus, the present invention is extremely useful for preventing or treating diseases wherein hypoadiponectinemia or the decreased expression of adiponectin in the adipose tissues is considered as a cause/index.

Next, Examples will further illustrate the present invention. They only explain the present invention and do not particularly limit the invention.

EXAMPLES

Synthetic Example 1

Synthesis of N-lauroyl-L-valine (Table 1, Compound 20)

294 g (2.51 mol) of L-valine was dissolved into 786 g of ion-exchange water, 358 g (2.42 mol) of an aqueous solution of 27% sodium hydroxide and 363 g of acetone. With stirring the solution, 533 g (2.43 mol) of lauroyl chloride and 358 g (2.47 mol) of an aqueous solution of 27% sodium hydroxide were simultaneously added dropwise thereto so that pH=12±0.2 and the temperature is kept at 19 to 20° C. After completion of the addition, the solution was stirred at 20° C. for 60 minutes. Then, it was heated up to 40° C., and 171 g of 75% sulfuric acid was added thereto in order to adjust pH=1.5. The layers of the oily substance and water phase that separated at 60° C. were split, and 1950 g of warm water of 60° C. was added to the oily substance. After the mixture was cooled down to 20° C., the precipitated solid substance was filtered out and washed with water. Then, the substance was vacuum-dried at 50° C. to obtain 710 g of N-lauroyl-L-valine (2.37 mol, yield 98%).

1H-NMR (CDCl$_3$, 300 MHz) δ (ppm) 0.88 (3H, t, J=6.8 Hz), 0.96 (3H, d, J=6.6 Hz), 0.99 (3H, d, J=6.6 Hz), 1.20-1.40 (16H, br), 1.58-1.74 (2H, br-m), 2.18-2.34 (3H, m), 4.58 (1H, dd, J=4.8 Hz, 8.4 Hz), 6.00 (1H, d, J=8.4 Hz), 7.4-8.6 (1H, br)

ESI-MS [M+H]+300

Synthetic Example 2

Synthesis of N-lauroyl-L-valine cyclohexylamide (Table 1, Compound 23)

61 mg (0.20 mmol) of N-lauroyl-L-valine and 39 mg (0.26 mmol) of N-hydroxysuccinimide monohydrate were dissolved into 3.0 mL of dried chloroform. 50 mg (0.26 mmol) of 1-ethyl-3-(3-dimethylaminopropyl)carbodiimide hydrochloride was added thereto under argon atmosphere and in the ice bath, and stirred at 0° C. for 3 hours. 35 μL of triethylamine and 35 μL of cyclohexylamine were added thereto and stirred at room temperature overnight. Then, 20 mL of ethyl acetate was added thereto and washed with 25 mL of 0.2N hydrochloric acid, 20 mL of water and 20 mL of a saturated aqueous solution of sodium hydrogen carbonate. The mixture was then dried with anhydrous sodium sulfate and condensed under reduced pressure. The residue was purified with a thin-layer chromatography (silica gel, chloroform:methanol=20:1) to obtain 34 mg of N-lauroyl-L-valine cyclohexylamide (0.089 mmol, yield 44%).

1H-NMR (CDCl$_3$, 300 MHz) δ (ppm) 0.88 (3H, t, J=6.8 Hz), 0.94-0.97 (6H, d*2), 1.08-1.44 (20H, m), 1.55-1.76 (6H, m), 1.80-1.96 (2H, m), 1.96-2.10 (1H, m), 2.21 (2H, t, J=7.8 Hz), 3.65-3.85 (1H, m), 4.15 (1H, dd, J=7.2 Hz, 9.0 Hz), 5.95 (1H, d, J=6.9 Hz), 6.22 (1H, d, J=8.7 Hz)

ESI-MS [M+H]+381

Examples 1 to 31

3T3-L1 cells were suspended in Dulbecco's Modified Eagle Medium (GIBCO, 12430-054) containing 10% fetal bovine serum to become $1.5 \times 10^5$ cells/mL and seeded. After the incubation in the CO$_2$ incubator at 37° C. for 72 hours, the medium was removed by suction. Then, the medium was exchanged for Dulbecco's Modified Eagle Medium containing 10 μg/mL of insulin, 1 μM of dexamethasone, 0.5 mM of IBMX (3-isobutyl-1-methylxanthine) and 10% fetal bovine serum, and further incubated in the CO$_2$ incubator at 37° C. for 48 hours. The test compound was added to the medium, and then the incubation was continued for 72 hours.

Eu (Europium) chelate labeling of anti-mouse adiponectin antibody (AF1119, by R&D Systems) was conducted by using 100 μg of LANCE Eu-W1024-ITC chelate (AD0013 by Perkin Elmer), which is a Eu chelate labeling reagent, to 200 μg of the antibody in accordance with the method described in the manual of the manufacturer. Biotin labeling of anti-mouse adiponectin antibody (AF1119, by R&D Systems) was conducted by using 26.8 μg of NHS-Biotin (1418165, Biotin Labeling Kit, by Boehringer Mannheim), which is a biotin labeling reagent, to 100 μg of the antibody in accordance with the method described in the manual.

The amount of adiponectin in the cell culture supernatant was measured as follows. The culture supernatant was diluted fivefold with TBS (Tris-buffered saline; 20 mM Tris-HCl pH 7.4, 0.15M NaCl) containing 0.1% bovine serum albumin (BSA), and 10 μL thereof was mixed with 300 ng/mL of the Eu chelate labeled antibody, 300 ng/mL of the biotin labeled antibody, 2.5 μg/mL of Streptavidin-APC (AD0201, by Perkin Elmer) and 10 μL of a TBS solution containing 0.1% BSA on the 384-well plate. After preserving the mixture at room temperature for 2 days, LANCE count was measured by using ARVO-SX multilabel counter (by Perkin Elmer) in accordance with the protocol of the LANCE method. At the same time, the mouse adiponectin preparation (8060-K, by LINCO) was also measured, and the concentration of adiponectin in the culture supernatant was calculated from the calibration curve of the preparation.

In the table, for example, when R2 and R3 are Val, R2 is a group of —CH(CH$_3$)$_2$ and R3 is a hydrogen atom. As for the adiponectin output in the table, those of Examples 8, 12, 13, 16, 17, 18, 19, 21, 22, 23 and 24 are indicated as the adiponectin concentration in the culture supernatant when adding each test compound in the concentration of 7 μg/mL, and those of other Examples are indicated as the adiponectin concentration in the culture supernatant when adding each test compound in the concentration of 12.5 μM.

Since the adiponectin output in the control groups without the compounds of the present invention is 24 ng/mL, it is seen that the compounds of the present invention can induce and/or promote the secretion of adiponectin.

Examples 32 to 44

Adiponectin outputs were measured by the same method as that of Examples 1 to 31.

TABLE 1

Acyl   AA

| Example | Acyl | | | AA | | | | | Adiponectin output (ng/ml) |
|---|---|---|---|---|---|---|---|---|---|
| | n | R5 R | R1 | D/L | R2 | R3 | X | R4 | |
| 1 | 6 | CH3 | H | L | Val | | O | H | 70 |
| 2 | 7 | CH3 | H | L | Ile | | O | H | 58 |
| 3 | 7 | CH3 | H | L | Leu | | O | H | 42 |
| 4 | 7 | CH3 | H | L | Val | | O | H | 64 |
| 5 | 8 | CH3 | H | L | Ile | | O | H | 74 |
| 6 | 8 | CH3 | H | L | Leu | | O | H | 54 |
| 7 | 8 | CH2=CH— | H | L | Leu | | O | H | 61 |
| 8 | 8 | CH2=CH— | H | L | Phe | | O | H | 54 |
| 9 | 8 | CH3 | H | L | Val | | O | H | 81 |
| 10 | 8 | CH2=CH— | H | L | Val | | O | H | 59 |
| 11 | 9 | CH3 | H | L | Leu | | O | H | 45 |
| 12 | 9 | CH3 | H | L | Phe | | O | H | 58 |
| 13 | 10 | CH3 | H | DL | Ala | | O | H | 53 |
| 14 | 10 | CH3 | H | L | Ile | | O | H | 84 |
| 15 | 10 | CH3 | H | L | Leu | | O | H | 67 |
| 16 | 10 | CH3 | H | DL | Me | Et | O | H | 78 |
| 17 | 10 | CH3 | H | — | Me | Me | O | H | 81 |
| 18 | 10 | CH3 | H | DL | Me | i-Pro | O | H | 87 |
| 19 | 10 | CH3 | H | L | Met | | O | H | 71 |
| 20 | 10 | CH3 | H | L | Val | | O | H | 92 |
| 21 | 10 | CH3 | H | DL | Val | | NH | H | 70 |
| 22 | 10 | CH3 | H | DL | Val | | NH | n-C12H25 | 64 |
| 23 | 10 | CH3 | H | DL | Val | | NH | cyclohexyl | 65 |
| 24 | 10 | CH3 | C2H5 | L | Val | | O | H | 66 |
| 25 | 12 | CH3 | H | L | Ile | | O | H | 93 |
| 26 | 12 | CH3 | H | L | Leu | | O | H | 56 |
| 27 | 14 | CH3 | H | L | Leu | | O | H | 57 |
| 28 | 14 | CH3 | H | L | Val | | O | H | 31 |
| 29 | 16 | CH3 | H | L | Leu | | O | H | 43 |
| 30 | 16 | CH3 | H | L | Val | | O | H | 43 |
| 31 | 20 | CH3 | H | L | Val | | O | H | 42 |

TABLE 2

Acyl  AA

| Exam. | Acyl R5 | | R1 | D/L | AA R2 | R3 | X | R4 | Adiponectin Ratio to Exam. 20 of Table 1 |
|---|---|---|---|---|---|---|---|---|---|
| | n | R | | | | | | | |
| 32 | 8  | CH3 | H | L  | t-Bu                | H  | O | H | 56%  |
| 33 | 10 | CH3 | H | L  | t-Bu                | H  | O | H | 103% |
| 34 | 10 | CH3 | H | DL | —CH(CF3)2           | H  | O | H | 25%  |
| 35 | 10 | CH3 | H | L  | allo-Ile            |    | O | H | 83%  |
| 36 | 10 | CH3 | H | L  | phenyl              | H  | O | H | 33%  |
| 37 | 10 | CH3 | H | L  | p-methoxyphenylmethyl | H | O | H | 46% |
| 38 | 10 | CH3 | H | DL | o-methylphenylmethyl | H | O | H | 31%  |
| 39 | 10 | CH3 | H | L  | cyclohexyl          | H  | O | H | 41%  |
| 40 | 10 | CH3 | H | L  | diphenylmethyl      | H  | O | H | 14%  |
| 41 | 10 | CH3 | H | DL | phenylmethyl        | Me | O | H | 22%  |
| 42 | 10 | CH3 | H | L  | p-chlorophenylmethyl | H | O | H | 44%  |
| 43 | 10 | CH3 | H | L  | 3-benzothienylmethyl | H | O | H | 20%  |
| 44 | 10 | CH3 | H | —  | —(CH2)6—            |    | O | H | 32%  |

In the table, —(CH2)6-indicates that R2 and R3 bond each other and form a cyclohexane ring. The adiponectin output of each compound in the table is indicated as the ratio thereof to that of Example 20 in Table 1.

Example 45

Male ob/ob mice of 5 weeks old (purchased from Charles River Laboratories Japan, Inc.) were preliminarily fed for one week by an experimental diet containing 25% by weight ratio of fats. Then, they were divided into groups so that their body weights and blood glucose were the same between the groups. After the division, N-lauroyl-L-valine (500 mg/kg) was orally administered once a day, and a control group was set, to which vehicle was administered. Taking into consideration the possibility that the effect of N-lauroyl-L-valine depends on the diet intake, pair-feeding group was also set as a control group in addition to the vehicle administered group, to which vehicle was daily administered in an average diet intake per a day of the N-lauroyl-L-valine administered group and, therefore, the diet intake thereof is quite the same as that of the N-lauroyl-L-valine administered group during the test period. The non-fasting blood glucose was measured on the 6th, 14th and 26th day after starting the administration. The blood glucose was measured by collecting 6 μL of the blood from the caudal vein and using a Fuji DriChem system (produced by FUJIFILM Medical Co., Ltd.). On the 26th day after starting the administration, the blood was collected by retroorbital bleeding, and 5 μL of its blood was used to conduct the measurement of glycated hemoglobin with the analyzer (HLC-723 GHbV, by Tosoh Technosystem). Further, on the 27th day after starting the administration, the blood was collected by retroorbital bleeding, and the insulin and triglyceride concentrations in plasma were measured. The measurement of the insulin concentration in plasma was conducted by using an insulin measurement kit (by Morinaga Institute of Biological Science, Inc.). The measurement of the triglyceride concentration in plasma was conducted by using a Fuji DriChem system. On the 38th day after staring the administration, autopsy was conducted to collect the liver of the mouse. Then, total RNA was extracted from the frozen liver by using ISOGEN (by Nippon Gene Co., Ltd.), and 0.5 μg of total RNA, oligo (dT) (by Invitrogen) and SuperScript III reverse transcriptase (by Invitrogen) were used to prepare cDNA. SYBER GREEN Master Mix (ABI) and a primer for amplifying uncoupling protein 2 (UCP2) gene, acyl-CoA oxidase (ACO) gene or glyceraldehyde-3-phosphate dehydrogenase (GAPDH) gene were added to cDNA corresponding to 7.5 ng of total RNA, and the gene expression level was measured with ABI 7700 detector. The expression levels of UCP2 and ACO genes were amended by being divided by the expression level of GAPDH mRNA. Two kinds of primers for amplifying UCP2 gene were used wherein the base sequences were ggcctctggaaagggactt and tgtcatgaggttggctttca from 5'. Similarly, two kinds of primers for amplifying ACO gene were used wherein the base sequences were gccaatgctggtatcgaagaa and ggaatcccactgctgtgagaa from 5', and two kinds of primers for amplifying GAPDH gene were used wherein the base sequences were gaggaccaggttgtctcctg and atgtaggccatgaggtccac from 5' (by Sigma-Aldrich Japan K.K.). As for the used primers, agarose gel electrophoresis was conducted after the PCR reaction to confirm the generation of the object product.

Figure 1:
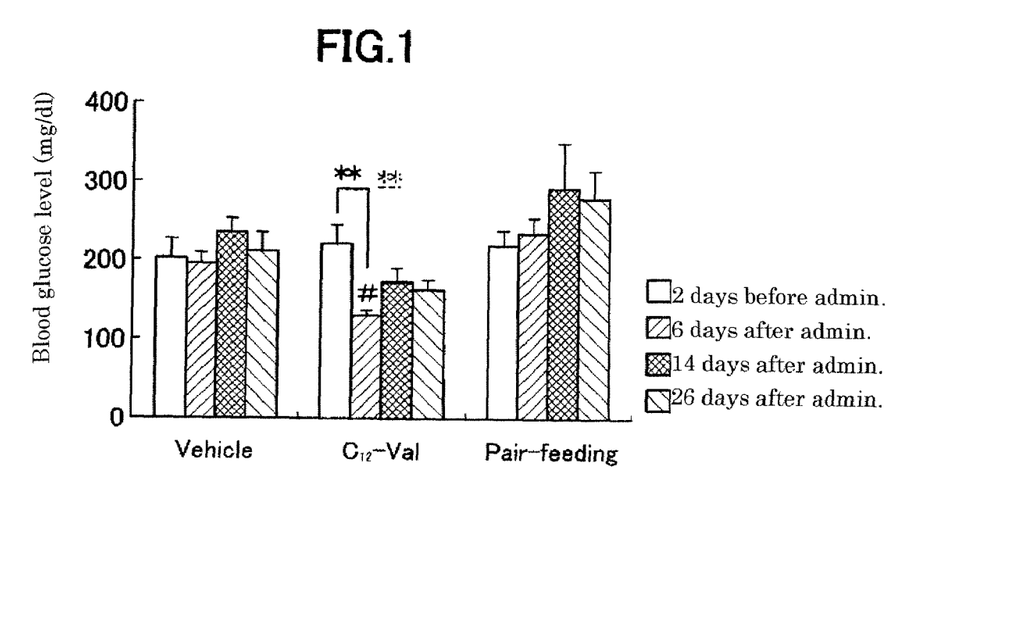
FIG. 1 shows a graph which indicates changes of the non-fasting blood glucose of each experimental group in Example 45 (average value±standard error, each group N=6). In the figure, the vertical axis indicates the non-fasting blood glucose level measured in the method mentioned in the specification (**: p<0.01, tested by the paired-t test; ##: p<0.01, difference from the vehicle group is tested by Tukey-Kramer method). Vehicle: vehicle administered group, C12-Val: N-lauroyl-L-valine administered group, Pair-feeding: pair-fed group with N-Lauroyl-L-valine administered group.
Figure 2:
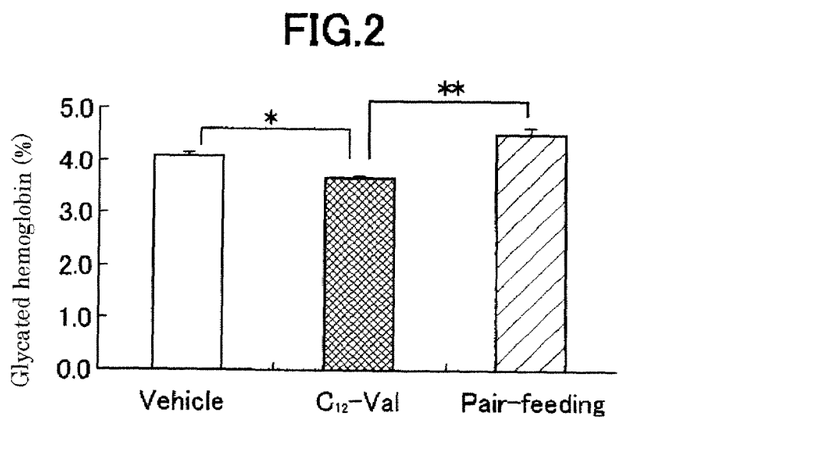
FIG. 2 shows a graph which indicates a glycated hemoglobin level of each experimental group in Example 45 on the 26th day after starting the administration (average value±standard error, each group N=6). The glycated hemoglobin level was measured in the method mentioned in the specification (*: p<0.05, **: p<0.01, tested by Tukey-Kramer method). Vehicle: vehicle administered group, C12-Val: N-lauroyl-L-valine administered group, Pair-feeding: pair-fed group with N-Lauroyl-L-valine administered group.
Figure 3:
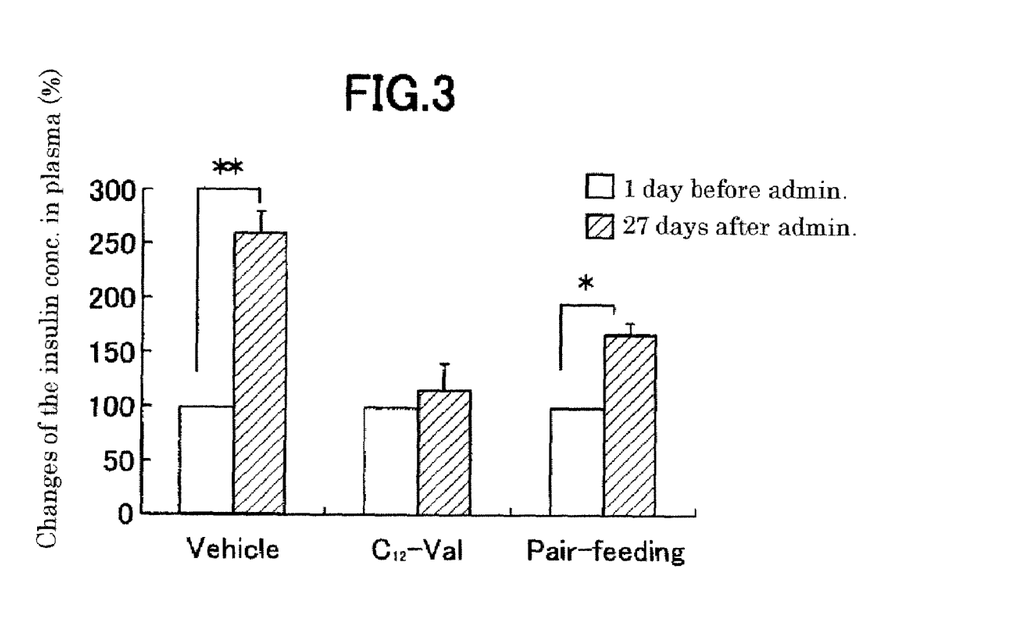
FIG. 3 shows a graph which indicates changes of the fasting insulin concentration in plasma of each experimental group in Example 45 before and after the test period (average value±standard error, each group N=6). The insulin concentration in plasma was measured in the method mentioned in the specification (**: p<0.01, *: p<0.05, tested by the paired-t test). Vehicle: vehicle administered group, C12-Val: N-lauroyl-L-valine administered group, Pair-feeding: pair-fed group with N-Lauroyl-L-valine administered group.
Figure 4:
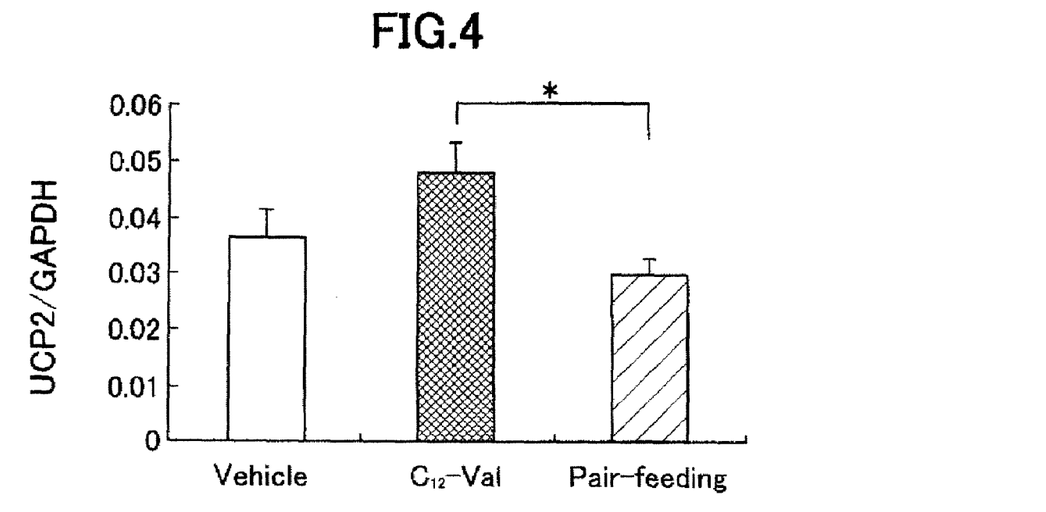
FIG. 4 shows a graph which indicates the measurement results of UCP2 mRNA expression level in the liver collected at autopsy in Example 45 (average value±standard error, vehicle group N=6, other groups N=5). UCP2 mRNA was measured in the method mentioned in the specification (*: $p<0.05$, tested by Student's-t test). Vehicle: vehicle administered group, C12-Val: N-lauroyl-L-valine administered group, Pair-feeding: pair-fed group with N-Lauroyl-L-valine administered group.
Figure 5:
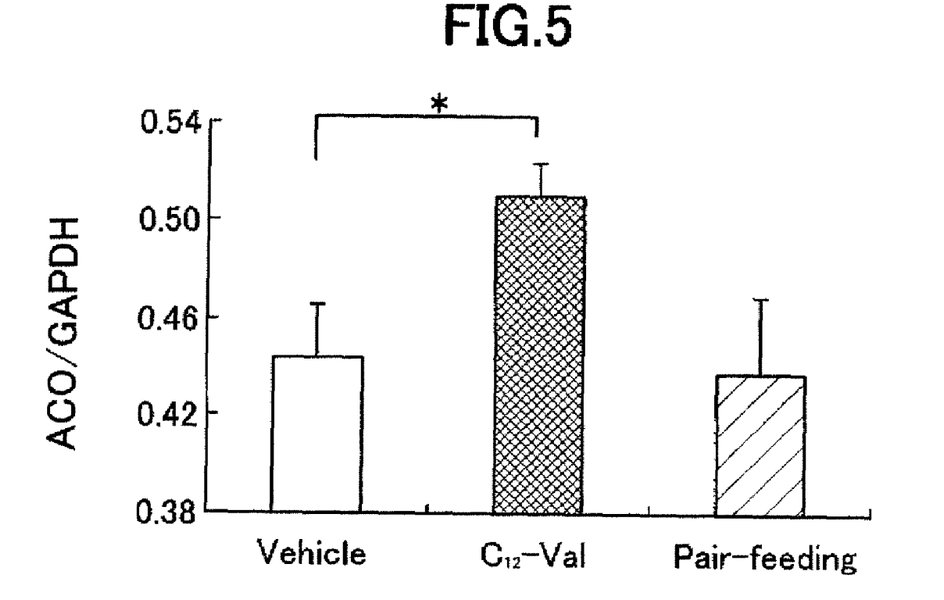
FIG. 5 shows a graph which indicates the measurement results of ACO mRNA expression level in the liver collected at autopsy in Example 45 (average value±standard error, vehicle group N=6, other groups N=5). ACO mRNA was measured in the method mentioned in the specification (*: $p<0.05$, tested by Student's-t test). Vehicle: vehicle administered group, C12-Val: N-lauroyl-L-valine administered group, Pair-feeding: pair-fed group with N-Lauroyl-L-valine administered group.
Figure 6:
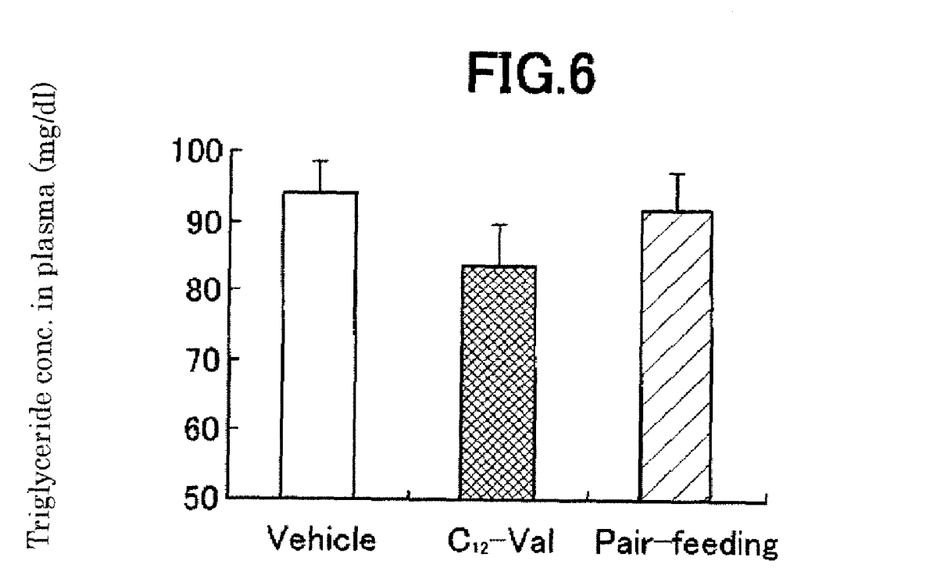
FIG. 6 shows a graph which indicates the triglyceride concentration in plasma in Example 45 on the 27th day after starting the administration (average value±standard error, each group N=6). In the figure, the vertical axis indicates the triglyceride concentration in plasma measured in the method mentioned in the specification.

As shown in FIG. 1, the blood glucose during the test period decreased only in the N-lauroyl-L-valine administered group as compared with the blood glucose before starting the administration and, therefore, the hypoglycemic action was seen by administration of N-lauroyl-L-valine. As shown in FIG. 2, a glycated hemoglobin level that is an index of diabetic treatment was significantly lower in the N-lauroyl-L-valine administered group than those of the vehicle group and the pair-feeding group. Thus, it was thought that administration thereof has a possibility to have a therapeutic effect of diabetes. Further, as shown in FIG. 3, the fasting insulin concentration in plasma that is known as an index of insulin resistance increased in the control groups after starting the administration, while such increase was not seen in the N-lauroyl-L-valine administered group. Thus, the effect of prevent- ing insulin resistance from deterioration was seen by administration of N-lauroyl-L-valine. As shown in FIGS. 4 and 5, the expressions of UCP2 and ACO of the liver, each of which is an important protein relating to lipid degradation, significantly increased due to the administration of N-lauroyl-L-valine as compared with the control groups, and, therefore, the action of promoting lipid degradation was seen by administration thereof. Actually, as shown in FIG. 6, the triglyceride concentration in plasma tended to be lower in the N-lauroyl-L-valine administered group than in the control groups. From the above, it was thought that administration of N-lauroyl-L-valine has a possibility to have an improving effect of hyperlipemia.

What is claimed is:

1. An acylamide compound of the following structural formulae, or pharmaceutically acceptable salt thereof:

Formula 4

Formula 5

Formula 7

Formula 8

Formula 9

Formula 10

Formula 11

-continued

Formula 12

Formula 13

Formula 17

Formula 18

2. An acylamide compound, or pharmaceutically acceptable salt thereof, of formula (1):

Formula (1)

wherein
R1 is a hydrogen atom;
R3 is a hydrogen atom;
R4 is a hydrogen atom;
X is an oxygen atom;
R5 is a straight-chain alkyl group having 5 to 21 carbon atoms which may have one double bond; and
R2 is either one of the following substituents:
2,2,2,2',2',2'-hexafluoroisopropyl group;
cyclohexyl group; or
diphenylmethyl group.

3. A food comprising the acylamide compound, or pharmaceutically acceptable salt thereof, according to claim 1.

4. A beverage comprising the acylamide compound, or pharmaceutically acceptable salt thereof, according to claim 1.

5. A food comprising the acylamide compound, or pharmaceutically acceptable salt thereof, according to claim 2.

6. A beverage comprising the acylamide compound, or pharmaceutically acceptable salt thereof, according to claim 2.

* * * * *

UNITED STATES PATENT AND TRADEMARK OFFICE
CERTIFICATE OF CORRECTION

PATENT NO.        : 7,732,637 B2
APPLICATION NO.   : 11/835029
DATED             : June 8, 2010
INVENTOR(S)       : Katsumi Maezono et al.

Page 1 of 3

It is certified that error appears in the above-identified patent and that said Letters Patent is hereby corrected as shown below:

Please delete claim 1 in its entirety and insert:

-- An acylamide compound of the following structural formulae, or pharmaceutically acceptable salt thereof:

Formula 4

Formula 5

Formula 7

Signed and Sealed this
Fifth Day of July, 2011

David J. Kappos
*Director of the United States Patent and Trademark Office*

CERTIFICATE OF CORRECTION (continued)
U.S. Pat. No. 7,732,637 B2

Formula 8

Formula 9

Formula 10

Formula 11

Formula 12

Formula 13

Formula 17

Formula 18.